United States Patent [19]

Mosbach et al.

[11] 4,415,665

[45] Nov. 15, 1983

[54] METHOD OF COVALENTLY BINDING BIOLOGICALLY ACTIVE ORGANIC SUBSTANCES TO POLYMERIC SUBSTANCES

[75] Inventors: Klaus H. Mosbach, Furulund; Kurt G. I. Nilsson, Lund, both of Sweden

[73] Assignee: Pharmacia Fine Chemicals AB, Uppsala, Sweden

[21] Appl. No.: 326,332

[22] Filed: Dec. 1, 1981

[30] Foreign Application Priority Data

Dec. 12, 1980 [SE] Sweden ................................. 8008776

[51] Int. Cl.$^3$ ...................... C12N 11/12; C12N 11/10; C12N 11/08
[52] U.S. Cl. .................................. 435/179; 435/178; 435/180
[58] Field of Search ............... 435/174, 176, 178, 179, 435/180, 181, 182

[56] References Cited

U.S. PATENT DOCUMENTS

3,959,079  5/1976  Mareschi et al. .................... 435/179
3,969,287  7/1976  Jaworek et al. ................. 435/181 X

OTHER PUBLICATIONS

Weliky et al., The Chemistry and Use of Cellulose Derivatives for the Study of Biological Systems, Immunochemistry, vol. 2, 1965 (pp. 293-312).

*Primary Examiner*—David M. Naff
*Attorney, Agent, or Firm*—Fred Philpitt

[57] ABSTRACT

The invention relates to a method of coupling organic ligands to a polymeric carrier. The organic ligand contains at least one primary or secondary amino group, at least one thiol group and/or at least one aromatic hydroxy group, and the polymeric carrier contains at least one hydroxy group. According to the invention the coupling is performed by forming a reactive derivative of the polymeric carrier by treatment with a sulfonyl halogenid, and reacting the formed reactive derivative with the organic ligand, which is thereby bonded directly to a carbon atom in the polymeric carrier. The polymeric carrier can, for example, be a possibly cross-linked polysaccharide, and the organic ligand is preferably a biological material such as a protein. The coupling product can, for example, be used for immunologic determinations, for affinity chromatography, etc. The coupling method can be performed under mild conditions not damaging sensitive organic ligands.

13 Claims, No Drawings

METHOD OF COVALENTLY BINDING BIOLOGICALLY ACTIVE ORGANIC SUBSTANCES TO POLYMERIC SUBSTANCES

The present invention relates to a new method of covalently binding organic substances, herein called "ligands", to polymeric substances, herein called "carriers". More specifically the invention relates to a new method of covalently binding organic ligands of the type containing one or more of the functional groups primary and secondary amino groups, thiol groups and aromatic hydroxy groups, to a carrier of the type polymeric substance which contains at least one hydroxy group.

In the prior art there are disclosed several methods for coupling biologically active ligands to water-insoluble carriers containing hydroxy groups. These methods have, among other things, been used for binding e.g. proteins such as enzymes, antibodies, and antigens to solid carriers. Such coupling products have found use in many different fields of technology. One example thereof is in connection with immunologic determination methods, wherein e.g. antibodies or antigen have been bonded to water-insoluble polymeric carriers. Another important application is in connection with affinity chromatography, wherein organic ligands having biospecific affinity to some other organic substance have been bonded to water-insoluble polymeric carriers. Water-insoluble polymers have also been bonded to, for example, proteins for modifying the properties thereof.

The coupling of the ligand to the carrier is often carried out such that the carrier is activated by a reactive group, which is then reacted with the desired ligand. Examples of known activation methods are activation by means of cyanogen bromide (see e.g. GB Pat. No. 1,223,281), triazine (GB Pat. No. 1,183,257), epoxy compounds (L. Sundberg et al, J. Chrom. 90 (1974), p. 87–98), N-hydroxy succinimide (P. Cuatrecasas et al, Biochem. Vol. 11, No. 12 (1972), p. 2291–2298), and 1,1'-carbonyldiimidazol (G. S. Bethell et al, J. Biol. Chem., Vol. 254, No. 8 (1979), p. 2572–2574).

Although these prior art methods are useful in many situations they nevertheless have certain drawbacks. For example, it is in many cases necessary to conduct the coupling under conditions damaging sensitive organic ligands such as enzymes during the coupling. Another deficiency in many of the prior art methods is that the coupling products are not sufficiently stable upon storage or use, resulting in a non-desired loss of coupled ligands from the carrier (primarily by hydrolysis). Further, some prior art coupling methods may give rise to changed charge conditions for the organic ligand, for example by the formation of charged groups at their binding site during the coupling. This makes the product unsuitable for e.g. use for affinity chromatography purposes.

The present invention i.a. aims at eliminating or reducing the drawbacks of the prior art coupling methods, and it in particular aims at providing a stable and hydrolysis resistent binding between the polymeric carrier and the organic ligand, which is covalently bonded directly to a carbon atom in the polymeric carrier. Another object of the present invention is to make said coupling possible under mild conditions not detrimentally affecting the reactants, in particular sensible biological ligands.

These and other objects of the invention are achieved by forming, in a method of the indicated type, a reactive derivative of a polymeric substance, which contains at least one hydroxy group bonded to a carbon atom, by activation of the hydroxy group or groups by means of an organic sulfonyl halogenide, and then reacting the reactive derivative with said amino group, tiol group and/or aromatic hydroxy group of the organic ligand.

The method according to the invention thus comprises an activation step, wherein a sulfonyloxy type leaving group is introduced into the polymeric carrier, and a coupling step, in which the organic ligand is bonded covalently to the polymeric carrier while splitting off the leaving group. These reactions, which preferably but not necessarily are carried out in two separate steps, can be illustrated as follows:

(1) Activation

$$PM\text{-}OH + Hal\text{-}SO_2\text{-}R \rightarrow PM\text{-}O\text{-}SO_2\text{-}R \tag{1}$$

In formula (1) PM signifies the polymeric substance or carrier, wherein the —OH— group is bonded to a carbon atom. Hal signifies halogen such as chlorine, bromine or iodine. For practical reasons chlorine is the preferred halogen. R signifies any organic group suitable for the sulfonyl chloride.

(2) Coupling

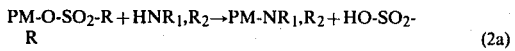
$$PM\text{-}O\text{-}SO_2\text{-}R + HNR_1,R_2 \rightarrow PM\text{-}NR_1,R_2 + HO\text{-}SO_2\text{-}R \tag{2a}$$

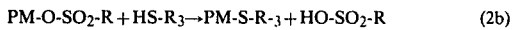
$$PM\text{-}O\text{-}SO_2\text{-}R + HS\text{-}R_3 \rightarrow PM\text{-}S\text{-}R_3 + HO\text{-}SO_2\text{-}R \tag{2b}$$

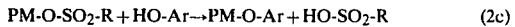
$$PM\text{-}O\text{-}SO_2\text{-}R + HO\text{-}Ar \rightarrow PM\text{-}O\text{-}Ar + HO\text{-}SO_2\text{-}R \tag{2c}$$

In these formulas PM and R have the same meaning as in formula (1) above. $R_1$ and $R_2$ (of which $R_1$ can be hydrogen) as well as $R_3$ and Ar signify, together with the amino, tiol and hydroxy function respectively, the organic ligand to be coupled, Ar indicating that the hydroxy group is aromatic.

The carrier PM can be a water-insoluble or water-soluble polymeric substance, and the choice of the carrier is not critical for carrying out the method according to the invention. In principle any type of carrier can be used, which has a polymeric nature and contains at least one hydroxy group bonded to a carbon atom and being available for activation and coupling. The carrier is chosen with regard to the requirements in the individual situation, primarily with regard to the type of ligand to be coupled and the intended use of the coupling product. The carrier may be comprised of natural, semi-synthetic or synthetic materials containing hydroxy groups, and in the first place such carriers come into question as have been used in the above indicated prior art coupling methods. Examples of important carrier materials are polysaccharides and polysaccharide containing materials, for example cellulose, agarose, dextran and cross-linked products thereof. Examples of synthetic carriers are polyhydroxyethylmethylacrylate and the like. It is, of course, also possible to use carriers which normally do not contain hydroxy groups, but which by suitable treatment can be provided with such groups. An example is silica particles, to the surface of which have been bonded groups containing at least one hydroxy group bonded to a carbon atom.

In accordance with the invention it is possible to vary the degree of activation of the carrier PM by the choice of the sulfonyl halogenid compound, i.e. by varying the group R. In this manner the choice of the sulfonyl halogenid compound can i.a. be adjusted to the reactivity or sensitivity of the organic ligand to be coupled, to the intended use of the coupling product, to possible need of storage of the activated derivative, etc. It is per se in the organic chemistry well known to convert hydroxy groups to leaving groups by means of sulfonyl halogenid compounds, as is the influence of various sulfonyl halogenid compounds on the degree of activation. Therefore, a person skilled in the art can easily select a suitable group R with regard to the needs and requirements in the individual situation. Examples of suitable groups R are p-tolyl, p-nitrophenyl, trifluoroethyl, trifluoromethyl, methyl, etc., but also many other aromatic and aliphatic groups R can successfully be used.

The coupling method according to the invention is generally applicable on organic ligands containing the indicated amino, thiol and/or aromatic hydroxy functions, and therefor $R_1$, $R_2$, $R_3$ and Ar can, in principle, signify any organic substance (aliphatic, aromatic, heterocyclic, heteroaromatic or combinations thereof) having said functional groups available for coupling. Of interest are in the first place such organic, especially biologically active ligands as have been used for coupling in the prior art methods mentioned above, for example proteins such as enzymes, antibodies and antigens, amino acids, thiol compounds, cofactors, nucleotides, polynucleotides, haptens and many other types of biologically active ligands, especially those having biospecific affinity to another substance and being suitable for e.g. affinity chromatographic purposes.

As mentioned above an important advantage of the coupling method according to the invention is that the coupled substance, i.e. the ligand, is covalently bonded directly to a carbon atom in the polymeric carrier, which makes splitting off by hydrolysis unlikely. Further, no extra charge is produced during the coupling, as is the case in most of the prior art coupling methods. Cross-linking of the carrier material is another common and undesired side effect of prior art coupling methods. This is avoided by means of the coupling method according to the invention.

As mentioned above the coupling according to the invention can be carried out under the most varying conditions as to temperature and pH, and it can be performed in aqueous reaction mediums as well as in inert organic solvents. The reaction conditions are not critical, neither for the activation step nor for the coupling step, but they are primarily chosen with regard to the sensitivity of the reactants and to practical considerations of convenience. It is, for example, often suitable to work at ambient temperature, and in the case of an aqueous reaction medium the pH is usually close to neutral pH. The degree of coupling to the OH groups of the carrier can usually be varied as needed, from utilizing essentially all OH groups to using only a small part thereof.

A few examples of how the invention can be practiced will be described in the following examples which, however, in no way are intended to limit the scope of the invention.

EXAMPLE 1

A. Activation of agarose with p-toluenesulfonyl chloride 7 g of water swollen agarose particles (Sepharose ®6B, available from Pharmacia Fine Chemicals AB, Uppsala, Sweden) were washed thoroughly with water, then with 3×70 ml of a mixture of water and dioxane (3:1 w/w), then with 3×70 ml of a mixture of water and dioxane (1:3 w/w), and finally thoroughly with anhydrous dioxane. The agarose particles treated in this way were transferred to a round bottom flask containing 1 g of p-toluenesulfonyl chloride dissolved in 2 ml of anhydrous dioxane. 1 ml of pyridine was then added dropwise during 1 minute while stirring. After reaction for 1 h at ambient temperature (20°–25° C.) the gel particles were at first washed with 300 ml of dioxane, and then with the above mentioned water/dioxane mixtures in reversed order. The gel particles were thoroughly washed with water and then stored in water at 4° C.

B. Coupling of alcohol dehydrogenase to activated agarose particles 1 g of the water swollen activated agarose particles of Example 1A above were washed with a 0.1 M aqueous solution of $NaHCO_3$ of pH 8.5 and were transferred to 0.3 ml of cold (4° C.) 0.1 M aqueous solution of $NaHCO_3$ of pH 8.5. This solution also contained 10 mg of the enzyme alcohol dehydrogenase. The reaction mixture was shaken for 25 h at ambient temperature (20°–25° C.). Then the gel particles were washed with 0.1 M aqueous solution of $NaHCO_3$ (pH 8.5), then with 0.5 M aqueous solution of NaCl, and finally with 0.1 M aqueous solution of sodium phosphate (pH 7.5). The amount of coupled alcohol dehydrogenase was measured by amino acid analysis to 112 mg per gram of dry particles. The coupling yield was 67%, based on the charged amount of enzyme. The specific activity of the coupled enzyme in relation to soluble enzyme was measured to 23%.

EXAMPLE 2

A. Activation of cross-linked agarose with 2,2,2-trifluoroethanesulfonyl chloride 1 g of water swollen particles of agarose cross-linked with glycerol ether bridges (Sepharose ®CL 6B, available from Pharmacie Fine Chemicals AB, Uppsala, Sweden) were washed well with water, thereafter with mixtures of water and acetone of increasing acetone contents, and finally thoroughly with anhydrous acetone. The treated agarose particles were transferred to a dry beaker provided with a stirrer. While stirring 0.2 ml of anhydrous acetone and 0.4 ml of pyridine and then 0.4 ml of 2,2,2-trifluoroethanesulfonyl chloride were added. After reaction for 10 minutes at ambient temperature (20°–25° C.) the gel particles were washed with acetone and then in sequence with mixtures of 1 mM aqueous solution of HCl and acetone in the proportions 20:80, 50:50, 70:30 and 85:15 w/w respectively. Finally, the particles were thoroughly washed with 1 mM aqueous solution of HCl and were stored in 1 mM aqueous solution of HCl at 4° C. The amount of sulfonate groups per gram of the dry product was calculated to 1.09 millimoles after analysis with regard to sulphur contents.

B. Coupling of trypsin to activated cross-linked agarose particles 1 g of the swollen activated agarose particles of Example 2A above were washed with 0.1 M aqueous solution of NaHCO$_3$ of pH 8.5, and 3 mg of trypsin were added, dissolved in 1 ml of cold aqueous solution which was 0.1 M with regard to NaHCO$_3$ and 0.5 M with regard to NaCl (pH 8.5).

The reaction mixture was shaken for 4 h at 4° C. The gel particles were then in sequence washed with 0.1 M aqueous solution of NaHCO$_3$ which also contained 0.5 M NaCl (pH 8.5), 0.5 M aqueous solution of NaCl, water, 0.1 M aqueous solution of sodium acetate (pH 4.0), 0.1 M aqueous solution of sodium acetate (pH 4.0) containing 0.5 M NaCl, and finally with 0.01 M aqueous solution of sodium acetate. The amount of coupled trypsin, as measured by amino acid analysis, was 34 mg per gram of the dry particles. The specific activity of the coupled enzyme compared to soluble enzyme was measured to 47%. The enzyme activity was determined with BAEE (1 mM) in 0.2 M sodium borate buffer, pH 8.1, at 253 nm in a cuvette with magnetic stirring at 4° C.

EXAMPLE 3

A. Activation of cellulose with 2,2,2-trifluoroethanesulfonyl chloride

Cellulose in powder form was treated with 1 M aqueous solution of NaOH at 20° C. for 1 h and was then in sequence washed with water, mixtures of water and dioxane with increasing dioxane contents, and finally with aqueous dioxane, 1 g of cellulose gave about 7 g of swollen gel in dioxane. 3 ml of anhydrous dioxane were added and then 0.4 ml of pyridine. 0.4 ml of 2,2,2-trifluoroethanesulfonyl chloride were added, and the mixture was in sequence stirred at 20° C. for 5 minutes. The activated cellulose product was washed in sequence with dioxane, mixtures of dioxane and 1 mM aqueous solution of HCl with increasing volume proportions of 1 mM HCl solution, and finally with 1 mM aqueous solution of HCl. 6 g of a swollen product were obtained, which was stored in 1 mM aqueous solution of HCl at 4° C.

B. Coupling of N$^6$-(6-aminohexyl)-adenosine-5'-monophosphate to activated cellulose particles 1 g of the swollen activated cellulose particles from Example 3A were washed with 0.1 M aqueous solution of NaHCO$_3$ (pH 8.5). 8 mg of N$^6$-(6-aminohexyl)-adenosine-5'-monophosphate (HAMP), dissolved in 0.5 ml of cold (4° C.) aqueous solution containing 0.2 M NaHCO$_3$ and 0.8 M NaCl, were added. The reaction mixture was shaken for 16 h at 4° C. Thereafter the gel particles were in sequence washed with 0.2 M aqueous solution of NaHCO$_3$, which also was 0.5 M with regard to NaCl, 0.5 M aqueous solution of NaCl, water, 0.01 M aqueous solution of HCl, and finally with 0.01 M aqueous solution of HCl, which was also 1 M with regard to KCl.

The amount of bonded HAMP as determined by UV analysis (on a sample washed with water) was 4.5 mg per gram of the swollen particles.

EXAMPLE 4

A. Activation of a derivative of porous silica gel using 2,2,2-trifluoroethanesulfonyl chloride 1 g of water swollen particles of porous silica gel substituted with —(CH$_2$)$_3$—O—CH$_2$—CH(OH)—CH$_2$OH groups (LiChrosorb ® available from Merck AG, Western Germany) were thoroughly washed with water, then with mixtures of water and acetone with increasing acetone contents, and finally thoroughly with anhydrous acetone. The treated silica particles were transferred to a dry beaker provided with a stirrer. While stirring 0.2 ml of anhydrous acetone and 0.4 ml of pyridine and then 0.4 ml of 2,2,2-trifluoroethanesulfonyl chloride were added. After reaction for 10 minutes at ambient temperature (20°-25° C.) the gel particles were washed with acetone and then in sequence with mixtures of 1 mM aqueous solution of HCl and acetone in the proportions 20:80, 50:50, 70:30 and 85:15 w/w respectively. Thereafter the gel particles were thoroughly washed with a 1 mM aqueous solution of HCl and were stored in 1 mM aqueous solution of HCl at 4° C.

B. Coupling of N$^6$-(6-aminohexyl)-adenosine-5'-monophosphate to activated silica particles 1 g of the swollen activated silica particles from Example 4A were washed with 0.1 M aqueous solution of NaHCO$_3$ (pH 8.5). 16 mg of N$^6$-(6-aminohexyl)-adenosine-5'-monophosphate (HAMP), dissolved in 0.5 ml of cold (4° C.) aqueous solution containing 0.2 M NaHCO$_3$ and 0.8 M NaCl, were added. The reaction mixture was then shaken for 16 h at 4° C. Thereafter the gel particles were in sequence washed with 0.2 M aqueous solution of NaHCO$_3$, which was also 0.5 M with regard to NaCl, 0.5 M aqueous solution of NaCl, water, 0.01 M aqueous solution of HCl, and finally with 0.01 M aqueous solution of HCl, which was also 1 M with regard to KCl.

The amount of bonded HAMP as determined by UV analysis (taken on a sample washed with water) was 17 mg per gram of the dry particles.

EXAMPLE 5

A. Activation of agarose with 2,2,2-trifluoroethanesulfonyl chloride

The activation was carried out on Sepharose ®4B (available from Pharmacia Fine Chemicals AB, Uppsala, Sweden) in accordance with Example 2A, but using 0.022 ml of pyridine and 0.011 ml of 2,2,2-trifluoroethanesulfonyl chloride. The amount of sulfonate groups per gram of the dry end product was calculated to 0.37 mM after analysis with regard to sulphur contents.

B. Coupling of protein A from Staphylococcus aureus to agarose particles

The coupling to the activated agarose particles from step A above was performed in accordance with Example 2B, using 3 mg of protein A for 4 h at 25° C. The amount of coupled protein A was measured by amino acid analysis to 86 mg per gram of dry particles.

C. Affinity chromatography of immunoglobuline G (IgG) on agarose particles coupled with protein A The agarose particles coupled with protein A from step B above were packed between two adapters in a glass column ($\phi = 1.6$ cm) equipped with pump and UV-monitor. The particles were equilibrated with buffer A (2% glycine-HCl, 0.4% NaCl, pH 7.0) and then the sample, consisting of 100 mg of IgG dissolved in 10 ml of buffer A, was applied on the column. Non-specifically bonded IgG was washed away by elution with 50 ml of buffer A. The specifically bonded IgG was desorbed with 25 ml of buffer B (0.1 M glycine-HCl, pH 3). The flow rate was 10 ml/h during the entire test. The eluate containing IgG was collected and measured spectrophotometrically at 280 nm. The amount of desorbed IgG was calculated to 9.1 mg from the absorbance value.

What we claim is:

1. A method of covalently binding
   (a) a biologically active organic substance that contains at least one substituent selected from the group consisting of
   primary and secondary amino groups,
   thiol groups, and
   aromatic hydroxy groups directly to a
   (b) polymeric substance (PM) containing at least one hydroxy group, comprising the steps of:
   (1) first forming a reactive derivative PM-O-SO$_2$-R by reacting
      (i) an organic sulfonyl halogenide of the formula Hal-SO$_2$-R, with
      (ii) a polymeric substance (PM) containing at least one hydroxy group,
         wherein R is an organic group and Hal is halogen, and
         wherein said at least one reacting hydroxy group is bonded to carbon atoms in the polymeric substance (PM), and then
   (2) reacting said reactive derivative PM-O-SO$_2$-R directly with the biologically organic substance as set forth in (a).

2. A method according to claim 1 wherein said polymeric substance (PM) is a polysaccharide or a derivative thereof.

3. A method according to claim 1 wherein said polymeric substance (PM) is cross-linked.

4. A method according to claim 1 wherein said biologically active organic substance of (a) exhibits biospecific affinity to another substance.

5. A method according to claim 1 wherein said biologically active organic substance of (a) is a polypeptide or a protein.

6. A method according to claim 1 wherein said biologically active organic substance (a) is selected from the group consisting of enzymes, antibodies, antigens, nucleotides, polynucleotides and haptens.

7. A method according to claim 1 wherein said polymeric substance is polysaccharide or polysaccharide containing materials.

8. A method according to claim 1 wherein said polymeric substance is agarose or cross-linked agarose.

9. A method according to claim 1 wherein said polymeric substance is dextran or cross-linked dextran.

10. A method according to claim 1 wherein said polymeric substance is cellulose.

11. A method according to claim 1 wherein said polymeric substance is silica particles containing at least one hydroxy group bonded thereto.

12. A method according to claim 1 wherein said sulfonyl halogenide is selected from the group consisting of
    p-toluensulfonyl chloride and
    2,2,2-trifluoroethane sulfonylchloride.

13. A method according to claim 1 wherein said biologically organic substance is selected from the group consisting of alcohol dehydrogenase, trypsin, protein A from Staphylococcus aureus and $N^6$-(6-aminohexyl)-adenosine-5'-monophosphate.

* * * * *